(12) United States Patent
Chang

(10) Patent No.: US 6,853,705 B2
(45) Date of Patent: Feb. 8, 2005

(54) RESIDUAL MAP SEGMENTATION METHOD FOR MULTI-LEAF COLLIMATOR-INTENSITY MODULATED RADIOTHERAPY

(75) Inventor: Sha Chang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 90 days.

(21) Appl. No.: 10/402,528

(22) Filed: Mar. 28, 2003

(65) Prior Publication Data

US 2004/0190680 A1 Sep. 30, 2004

(51) Int. Cl.$^7$ .................................................. A61N 5/10
(52) U.S. Cl. ........................................................ 378/65
(58) Field of Search .......................................... 378/65

(56) References Cited

U.S. PATENT DOCUMENTS

| | | | |
|---|---|---|---|
| 4,726,046 A | 2/1988 | Nunan | 378/65 |
| 4,868,843 A | 9/1989 | Nunan | 378/152 |
| 4,868,844 A | 9/1989 | Nunan | 378/152 |
| 4,987,309 A | 1/1991 | Klasen et al. | 250/492.1 |
| 5,166,531 A | 11/1992 | Huntzinger | 250/505.1 |
| 5,663,999 A | 9/1997 | Siochi | 378/65 |
| 5,724,403 A | 3/1998 | Siochi et al. | 378/150 |
| 5,818,902 A * | 10/1998 | Yu | 378/65 |
| 5,889,834 A | 3/1999 | Vilsmeier et al. | 378/147 |
| 6,049,587 A | 4/2000 | Leksell et al. | 378/65 |
| 6,052,430 A | 4/2000 | Siochi et al. | 378/65 |
| 6,097,787 A | 8/2000 | Siochi | 378/65 |
| 6,108,400 A | 8/2000 | Siochi | 378/65 |
| 6,128,366 A | 10/2000 | Siochi | 378/65 |
| 6,134,296 A | 10/2000 | Siochi | 378/65 |

(List continued on next page.)

OTHER PUBLICATIONS

Chang et al., "Dose optimization via index–dose gradient minimization", Med. Phys. 29 (6), Am. Assoc. Phys. Med., p. 1130–1146 (Jun. 2002).

Potter et al., "A quality and efficiency analysis of the IMFAST™ segmentation algorithm in head and neck 'step & shoot' IMRT treatments", Med. Phys. 29 (3), Am. Assoc. Phys. Med., p. 275–283 (Mar. 2002).

Siochi, "Virtual micro–intensity modulated radiation therapy", Med. Phys. 27 (11), Am. Assoc, Phys. Med., p. 2480–2493 (Nov. 2000).

Chang et al., "Intensity modulation delivery techniques: "Step & shoot" MLC auto–sequence versus the use of a modulator", Med. Phys. 27 (5), Am Assoc. Phys. Med., p. 948–959, (May 2000).

Que, "Comparison of algorithms for multileaf collimator field segmentation", Med. Phys. 26 (11), Am. Assoc. Phys. Med., p. 2390–2396 (Nov. 1999).

(List continued on next page.)

Primary Examiner—Allen C. Ho
(74) Attorney, Agent, or Firm—Jenkins, Wilson & Taylor, P.A.

(57) ABSTRACT

In a method for sequentially generating segment fields for use in delivering intensity modulated radiotherapy an input continuous intensity map is generated. A segment field is generated directly from the input intensity map. A residual continuous intensity map is generated that is based on the respective photon fluence contributions from the input intensity map and a fractionally intensity map corresponding to the segment field. These steps are repeated for a number of iterations to generate a like number of additional segment fields and residual maps derived therefrom. In each iteration, the residual map generated in the previous iteration is used as the input intensity map.

33 Claims, 19 Drawing Sheets

U.S. PATENT DOCUMENTS

| | | | |
|---|---|---|---|
| 6,142,925 A | 11/2000 | Siochi et al. | 600/1 |
| 6,167,114 A | 12/2000 | Siochi | 378/65 |
| 6,240,161 B1 | 5/2001 | Siochi | 378/65 |
| 6,240,162 B1 | 5/2001 | Hernandez-Guerra et al. | 378/65 |
| 6,314,159 B1 | 11/2001 | Siochi | 378/65 |
| 6,330,300 B1 | 12/2001 | Siochi | 378/65 |
| 6,335,961 B1 | 1/2002 | Wofford et al. | 378/65 |
| 6,349,129 B1 | 2/2002 | Siochi | 378/65 |
| 6,353,655 B1 | 3/2002 | Siochi | 378/65 |
| 6,388,816 B2 | 5/2002 | Brown et al. | 359/641 |
| 6,449,335 B1 | 9/2002 | Siochi | 378/65 |
| 6,473,490 B1 | 10/2002 | Siochi | 378/65 |
| 6,477,229 B1 | 11/2002 | Grosser | 378/65 |
| 6,661,871 B2 * | 12/2003 | Siochi | 378/65 |
| 6,687,330 B2 * | 2/2004 | Hernandez-Guerra | 378/65 |
| 6,757,355 B1 * | 6/2004 | Siochi | 378/65 |
| 2003/0086530 A1 * | 5/2003 | Otto | 378/65 |

OTHER PUBLICATIONS

Chang et al., "A Comparison of Different Intensity Modulation Treatment Techniques for Tangential Breast Irradiation", Int. J. Radiation Oncology Biol. Phys., vol. 45, No. 5, p. 1305–1314 (1999).

Siochi, "Minimizing Static Intensity Modulation Delivery Time Using an Intensity Solid Paradigm", Int. J. Radiation Oncology Biol. Phys., vol. 43, No. 3, p. 671–680, (1999).

Xia et al., "Multileaf collimator leaf sequencing algorithm for intensity modulated beams with multiple static segments", Med. Phys. 25 (8), Am. Assoc, Phys. Med., p. 1424–1434 (Aug. 1998).

Webb, "Configuration options for intensity–modulated radiation therapy using multiple static fields shaped by a multileaf collimator. II: Constraints and limitations on 2D modulation", Phys. Med. Biol. 43, p. 1481–1495 (1998).

Bortfield et al., "X–Ray Field Compensation with Multileaf Collimators", Int. J. Radiation Oncology Biol. Phys., vol. 28, No. 3, p. 723–730 (1994).

Galvin et al., "Combining Multileaf Fields to Modulate Fluence Distributions", Int. J. Radiation Oncology Biol. Phys., vol. 27, p. 697–705 (1993).

* cited by examiner

RESIDUAL MAP SEGMENTATION METHOD FOR MULTI-LEAF COLLIMATOR-INTENSITY MODULATED RADIOTHERAPY

TECHNICAL FIELD

The present invention generally relates to intensity-modulated radiotherapy (IMRT). More particularly, the invention relates to the optimized configuration of multi-leaf collimator leaves for delivery of IMRT.

BACKGROUND ART

For any given radiation treatment procedure, a common goal is to deliver an adequate, therapeutically effective dosage of radiation to the tumor while minimizing potentially damaging dosage exposure to nearby critical organs and other tissues (termed organs at risk or OAR). Intensity-modulated radiotherapy (IMRT) is a popular new technology to customize radiation treatment in accordance with this goal for each patient. The most widely available apparatus for delivering IMRT procedures for cancer patients is a medical linear accelerator (LINAC). LINAC-based IMRT treatment apparatuses are described in, for example, U.S. Pat. Nos. 5,663,999; 6,134,296; 6,240,161; 6,240,162; 6,330,300; 6,335,961; 6,349,129; 6,353,655; 6,449,335; 6,473,490; and 6,477,229, the respective contents of which are incorporated herein in their entireties.

Compared to conventional LINAC-based radiotherapy treatments, an IMRT treatment delivers a variable intensity distribution, or intensity map, within a treatment portal. The intensity maps are normally designed by a dose optimization algorithm, whose objective is defined by the radiation oncologist for the patient to meet a set of dose distribution criteria. The criteria often involve the tumor volume and structures of nearby organs at risk (OAR). The intensity maps, sometimes along with other treatment parameters, are used as variables by the dose optimization algorithm to design the optimal treatment. The dose optimization algorithms generally are an integral part of treatment planning systems, and can be implemented in treatment planning software (TPS).

One difference in dose optimization algorithms is the resolution of the intensity map they generate, i.e., whether the intensity map is continuous or discrete. When the limitations of treatment delivery technique are taken into consideration in the dose optimization process, such as occurs in conventional multi-leaf collimator (MLC) treatment delivery techniques (described hereinbelow), the resulting intensity maps are discrete. When these limitations are not considered, the optimization can often produce continuous intensity maps that represent the ideal IMRT treatment. It has been demonstrated that the dosimetric quality of an actual IMRT treatment can be considerably affected by the resolution of the delivery technique compared to the ideal treatment. See Chang et al., Intensity modulation delivery techniques: "Step & shoot" MLC autosequence versus the use of a modulator, Med. Phys. 27, 948 (May 2000), the content of which is incorporated herein in its entirety; and Potter et al., A quality and efficiency analysis of the IMFAST™ segmentation algorithm in head and neck "step & shoot IMRT treatments, Med. Phys. 29 (3), 275–283 (March 2002), the content of which is incorporated herein in its entirety. See also Chang et al., Dose optimization via index-dose gradient minimization, Med. Phys. 29, 1130 (June 2002), the content of which is incorporated herein in its entirety.

Virtually all treatment planning systems, commercial or in-house, have implemented, or are in the process of doing so, dose optimization algorithms to design IMRT treatments. The three-dimensional TPS at the University of North Carolina at Chapel Hill, which is termed PlanUNC (PLUNC), has implemented the index-dose gradient minimization optimization algorithm developed by Chang et al., Dose gradient optimization, Med. Phys. 23, 1072 (1996), the content of which is incorporated herein in its entirety.

Once the dose optimization algorithm of PLUNC generates the ideal intensity maps, an example of which is shown in FIG. 1, further processing of this and other treatment information in preparation for actual delivery to the patient will depend on the particular IMRT delivery technique to be utilized. LINAC-based IMRT delivery techniques can generally be categorized into two types: compensator- or modulator-based and multi-leaf collimator- or MLC-based IMRT methods. Compensator-based techniques employ a compensator, or intensity modulator. The compensator is a physical beam attenuation device placed in the beam path of the radiation treatment apparatus during treatment. The compensator is customized to selectively attenuate the photon fluence and thus deliver the intended fluence distribution to the patient. The compensator-based technique delivers each IM field statically, i.e., the modulation does not vary with time during treatment. The modulation in the MLC-based IMRT techniques, however, varies in both time and space. Multi-leaf collimator (MLC) techniques utilize a built-in or added-on device of modern medical accelerators to deliver the intensity modulation. As appreciated by persons skilled in the art, an MLC device typically comprises at least two transversely opposing sets of radiation-blocking leaves that define the radiation field capture on a patient (see, e.g., leaves L in FIG. 11). The leaves of the respective leaf sets of the MLC device are movable toward and away from each other in order to define an opening or port through which the radiation beam is delivered to the patient.

The MLC techniques can be further categorized into two types: the "dynamic" or "sliding window MLC technique and the step-and-shoot" or "stop-and-shoot" technique. The dynamic MLC technique delivers an intensity modulated photon field by moving the collimator leaves during irradiation. The "step-and-shoot" MLC technique delivers an intensity modulated photon field via a sequence of static MLC ports. Each MLC configuration or the port opening defined thereby is termed a "segment" or "segment-field". The intended intensity map is delivered to the patient cumulatively in an MLC-based delivery technique. That is, the treatment of the IM field is delivered through the cumulative number of automatically sequenced segments or segment-fields.

The "step-and-shoot" MLC technique requires an MLC-IMRT segmentation algorithm to design the MLC leaf configuration and monitor units (MU's) for each segment based on the intended intensity map.

Most MLC sequence segmentation software products available now require discrete intensity maps to generate the segment-fields of "step & shoot" MLC-IMRT treatment. An example of a discrete intensity map is shown in FIG. 2. FIG. 3 illustrates a sequence of eight segments generated for the 5-IM-level map of FIG. 2, for the left lateral field of a sinus treatment. In the segment with the largest area, or base segment, a significant area of the left side can be seen to be blocked by the MLC leaves to minimize the radiation dosage to the eyes of the patient. MLC sequence optimization software systems, such as the IMFAST™ system commercially available from Siemens Medical Systems, Inc., Concord, Calif., take into account the mechanical constraints of the MLC leaf positioning, the "tongue and groove" effect, a simple photon source model fitted to the accelerator beam data, and other relevant parameters in the MLC sequence optimization. MLC sequence optimization software systems such as IMFAST™ make available several different sequence optimization methods, all of which strive to minimize the number of MLC segments and treatment delivery time, and strive to deliver the IM field as close to the inputted discrete IM map as possible. All segments of the same IM field can be grouped together and delivered automatically with a keyboard operation similar to the delivery of a single field.

The intensity map resolution yielded by the "step and shoot" MLC delivery technique has a significant effect on the efficiency and the quality of the IMRT treatment. The resolution of the intensity map can be considered as being represented by two resolutions. The first resolution is that of the intensity levels, i.e., the number of intensity steps that are used to synthesize the intensity map. The second is the spatial resolution of the intensity map. The intensity maps employed by the IMFAST™ system have a user-defined number of discrete intensity levels and a finite spatial resolution related to the width of each MLC leaf. In one study, it was shown that the quality of a dose-optimized IMRT treatment is directly related to the resolution of the intensity maps delivered by "step and shoot" treatments. See Chang et al., Intensity modulation delivery techniques: "Step & shoot" MLC auto-sequence versus the use of a modulator, Med. Phys. 27, 948 (May 2000). This study showed that when the smooth intensity maps originally generated by a dose optimization algorithm are truncated into corresponding discrete maps, a substantial deterioration in dose distributions can result-not only in the target but also in the nearby critical/normal structures. The treatment quality sometimes can be improved by increasing the intensity level resolution of the intensity map, but at the cost of increasing the number of segments required and thus reducing the efficiency of the treatment.

A recent technique has been developed to refine the intensity map resolution by effectively improving the spatial resolution of the technique from 1-cm×1-cm to 5 mm×5 mm by modification treatment hardware (smaller and more MLC leaves and treatment table shifts during treatment). However, this hardware solution has the drawback of increasing the mechanical complexity and thus the cost of the device.

Some of the available segmentation algorithms are designed to find the set of MLC segment-fields (and their corresponding MU values) for cumulatively delivering an intensity map that matches the input map as close as possible and requires the shortest treatment time. Unfortunately, the discreteness used in existing MLC-based IMRT dose optimization and segmentation algorithms is considerably stricter than the intrinsic limitations of the existing MLC delivery hardware. For instance, although the width of the MLC leaves is fixed, the position of each MLC leaf along its travel direction is continuously adjustable within its range of motion. In addition, the angular orientation of the MLC leaves, or the collimator angle, is continuously adjustable within its range of motion. It is proposed herein that these variables are degrees of freedom in the MLC segmentation. It is further proposed herein that, once properly utilized, these degrees of freedom can improve the segmental MLC technique to deliver a much finer-resolution intensity modulation with the same or better treatment efficiency. The angle of the collimator can have a significant influence of the discrepancy between the discrete "skyscraper" IM map and its corresponding original smooth map. The effect of the collimator angle is similar to that in conforming an MLC opening to a given treatment portal defined by a conventional block. An optimal collimator angle can minimize the jaggedness of the edge or contour of the field defined by the MLC opening. An optimal collimator angle can reduce the difference between the discrete IM map and its original smooth map. Therefore, it is proposed herein that the orientation of the MLC leaves or collimator angle should be considered as a variable in the MLC-IM treatment delivery optimization process.

A primary advantage of the MLC-IMRT delivery techniques over the modulator delivery techniques is treatment delivery automation. The compensator-based technique, however, has the advantage of high resolution of intensity modulation. In a comparative study of "step and shoot" MLC-IM and modulator-IM treatment techniques for two clinical cases, a three-field sinus tumor treatment and a six-field nasopharynx tumor treatment, the dose optimization quality of each treatment technique was judged by how well the defined optimization goal was reached for each case. See Chang et al., Intensity modulation delivery techniques: "Step & shoot" MLC auto-sequence versus the use of a modulator, Med. Phys. 27, 948 (May 2000). It was found that target dose uniformity initially improved quickly as the IM level increased to 5, then started to approach saturation when the MLC technique was performed. A linear proportionality was found between the number of IM levels used and the number of MLC segments required. For both clinical cases, the proportionality was between one to two segments per IM level per field. Both clinical cases suggested that an IM level of 5 offered a good compromise between the dose optimization quality and treatment irradiation time. In the absence of both space and intensity discreteness intrinsic to the MLC technique, the modulator-based technique produced greater tumor dose uniformity and normal structure sparing.

The segmental MLC technique also suffers from longer treatment irradiation time. Treatment irradiation time can be defined as the time elapsed between the initiation of a treatment on the console of a medical LINAC-based apparatus, such as by pushing a "RAD ON" button, to the completion of the irradiation. In addition to this treatment time, the compensator-based techniques and other conventional techniques such as wedge-based techniques require time for therapists to enter the treatment room to exchange the modulator or wedge between the application of different treatment fields. In order to render a meaningful inter-comparison of treatment irradiation time among the MLC-IM technique, the compensator-IM technique, and the wedge-based technique, an equivalent treatment irradiation time can be defined as the treatment irradiation time defined above plus the beam modifier exchange time when applicable. In the case of the MLC-IM technique, it has been found that the equivalent treatment irradiation time depends on the IM resolution or the IM level. Better dose optimization quality requires more IM levels, which in turn requires more treatment irradiation time. It has been further found that the modulator-IM and the wedge-based treatment technique requires substantially less treatment irradiation time. For the specific cases studied, the treatment time required by the MLC-IM technique was 100–400% longer than the conventional techniques. See Chang et al., Intensity modulation delivery techniques: "Step & shoot" MLC auto-sequence versus the use of a modulator, Med. Phys. 27, 948 (May 2000).

Therefore, in the case of segmental MLC-IMRT techniques, there is much room for improvement regarding intensity modulation quality and treatment delivery efficiency.

Treatment automation and intensity modulation resolution are both important considerations in IMRT treatment delivery. It would therefore be advantageous to provide a segmentation method that combines the strengths of both general types of delivery techniques, i.e., the treatment automation afforded by segmental MLC-IMRT techniques and the high-resolution intensity modulation afforded by compensator-IMRT techniques. It would also be advantageous to provide a segmentation method that takes full advantage of the degrees of freedom afforded by radiation treatment apparatuses equipped with MLC functionality. It would further be advantageous to provide a segmental MLC-IMRT technique that reduces treatment time.

SUMMARY OF THE INVENTION

A method is disclosed for generating a sequence of MLC segment-fields for intensity modulated radiotherapy without the use of discrete intensity maps, comprising the following steps. A segment field is generated directly from a continuous intensity map, such as an intensity map derived from a dose optimization. The segment field is generated by determining an optimal collimator configuration that corresponds to a contour of the continuous intensity map at a selected intensity level thereof. A fractional intensity map corresponding to the segment field generated is calculated. These steps are repeated for one or more iterations to generate one or more additional segment fields. For each iteration, the continuous intensity map used to determine the optimal collimator configuration of the additional segment field is derived in part from the fractional intensity map calculated in the previous iteration.

In one aspect of this method, the determination of the optimal collimator configuration comprises determining respective lateral positions of the collimator leaves that best conform to the contour of an upper opening of a selected map section. In another aspect, the determination of the optimal collimator configuration comprises determining an angle of the collimator leaves according to a first solution that best conforms to the contour of the upper opening of the selected map section. According to a further aspect, the determination of the optimal collimator configuration comprises determining an angle of the collimator leaves according to a second solution that best preserves a high gradient region of the continuous intensity map. According to yet another aspect, the collimator angle is determined by considering both the first and the second solutions.

Another method is disclosed for sequentially generating segment fields for use in delivering intensity modulated radiotherapy, comprising the following steps. An input continuous intensity map is generated, imported, or otherwise provided. The first input intensity map so provided is an ideal intensity map representing an ideal radiotherapy treatment. A segment field is generated directly from the input intensity map. A residual continuous intensity map is generated based on the respective photon fluence contributions from the input intensity map and a fractional intensity map corresponding to a segment field. These steps are repeated for a number of iterations to generate additional segment fields and residual maps derived therefrom. In each iteration, the residual map generated in the previous iteration is used as the input intensity map.

Yet another method is disclosed for sequentially generating segment fields for use in delivering intensity modulated radiotherapy, comprising the following steps. An input continuous intensity map derived from a dose optimization is divided into a plurality of map sections. Each map section spans an intensity range of the input intensity map. The map section corresponding to the lowest intensity range is selected, and a contour of an upper opening of the selected map section is defined. An optimal collimator configuration that best defines the contour of the upper opening of the selected map section is determined in order to configure a segment field corresponding to the optimal collimator configuration. A fractional continuous intensity map contributed by the segment field is calculated. The fractional intensity map is subtracted from the input intensity map to generate a residual continuous map. These steps are repeated for a number of iterations until one or more predetermined stopping criteria are met. In each iteration, the residual intensity map generated in the previous iteration is used as a new input intensity map to configure a new segment field and to generate a new residual intensity map.

The methods disclosed herein can be implemented by a suitable computer or other electronic processing means. Accordingly, a computer program product is provided that comprises computer-executable instructions embodied in a computer-readable medium for performing the steps of any of the methods disclosed herein.

It is therefore an object of the invention to provide a method for sequentially generating segment fields for use in delivering intensity modulated radiotherapy.

An object of the invention having been stated hereinabove, and which is addressed in whole or in part by the present invention, other objects will become evident as the description proceeds when taken in connection with the accompanying drawings as best described hereinbelow.

DETAILED DESCRIPTION OF THE INVENTION

The segmentation method disclosed herein is designed to fully utilize the functionalities of existing MLC hardware, and to minimize the effects of the intrinsic discreteness of the MLC-based delivery technique in intensity modulation generation. It is hypothesized herein that not every part of the intensity map has the same influence to the treatment dosimetry, or the closeness of the treatment dosimetry to the optimization objective. It is further hypothesized that intensity map regions exhibiting high gradients (i.e., the intensity changes drastically in space) have stronger influences on the closeness of the treatment result to the optimization objective than the regions of low gradients. It has been found that the high gradient regions of the intensity map often divide the planned treatment volume (PTV) and the nearby organ at risk (OAR). Hence, preserving this region of the map is crucial for the intended tumor coverage and OAR sparing. Therefore, when attempting to deliver intensity modulation as close as possible to that of the ideal treatment, the segmentation algorithm should concentrate its effort on the preservation of high gradient regions of the intensity map. The goal of the MLC segmentation method is to generate a sequence of MLC segment fields to deliver intensity modulation that is as close as possible to the continuous intensity modulation of the ideal IMRT treatment. The output of the segmentation process should include all information needed for the actual treatment delivery including segment-field configuration and corresponding MU values for the IMRT treatment of prescribed dose.

In the use of the method disclosed herein, preliminary results have shown considerable improvements in the treatment dosimetry with equal or better treatment efficiency in clinical cases studied compared to the IMFAST™ algorithm by Siemens. For instance, the present method can yield the same or better dose optimization quality than conventional methods while requiring less segment fields, thereby reducing treatment time.

Figure 4:
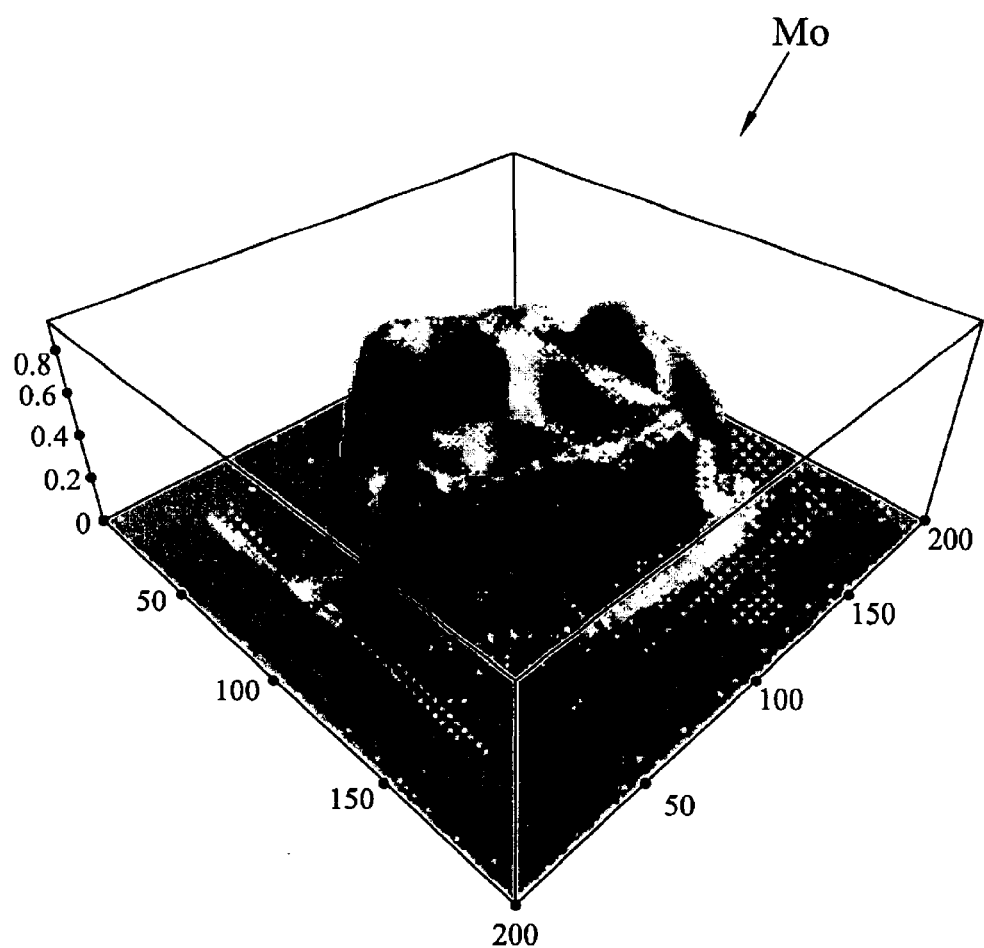
FIG. 4 is an example of an ideal intensity map inputted into the segmentation process disclosed herein.

In accordance with the method, a treatment dose optimization routine is performed to generate one or more continuous, smooth intensity maps representing the ideal treatment for a patient afflicted with a tumor. The number of intensity maps generated will depend on the number of treatment fields. An example of an ideal intensity map is shown in FIG. 4 and generally designated $M_0$.

Any number of types of treatment planning software (TPS) containing one or more dose optimization algorithms could be adapted for use with the present method. However, it is desirable for the dose optimization algorithm to design the intensity map without considering the treatment delivery device limitation. This way, ideal treatment using high-resolution intensity maps is generated and used for MLC segmentation. The result of the ideal treatment can be used as the gold standard to evaluate the quality of a deliverable MLC treatment. It is also desirable that the treatment planning system use a realistic photon source model for intensity map and MU calculation. Lastly, it is desirable for the treatment planning system to be capable of importing back the segment-fields and their MU values after segmentation, and computing the treatment dosimetry for comparison with the ideal IMRT treatment, although this capability is optional in regard to routine clinical applications. Moreover, in addition to the photon source model, the treatment planning system should be able to provide other information to the segmentation software, such as the geometry of the collimator design, for the purpose of intensity map and MU calculation. For a given TPS and MLC hardware combination, the accuracy of the photon source modeling, intensity map calculation, and MU calculation should be confirmed in the commissioning of the segmentation software. As one example of a suitable TPS program, the afore-described PLUNC TPS could be employed, preferably executing the afore-described index-dose gradient minimization algorithm.

Once dose optimization has been performed, the ideal intensity map or maps $M_0$ are imported from the TPS into segmentation software adapted to carry out the present method, along with any other pertinent treatment information such as information needed for the segmentation software to calculate all treatment parameters such as MU values. In one aspect of the method, the segmentation algorithm is separate from the dose optimization algorithm, although either the dose optimization algorithm alone or both algorithms could be integrated into or otherwise considered to be part of the TPS. There are advantages to separating the process of treatment dose optimization that design the intensity modulation maps and the process of finding the appropriate treatment parameters of the delivery technique. Through such separation, the dose optimization algorithm can concentrate on deriving the intensity maps needed to reach the optimization objective. Furthermore, the dose optimization algorithm establishes the optimized result of the ideal treatment-the benchmark which all deliverable treatments with actual limitations should approach.

Figure 1:
FIG. 1 is a smooth intensity map generated by a dose optimization process.
Figure 2:
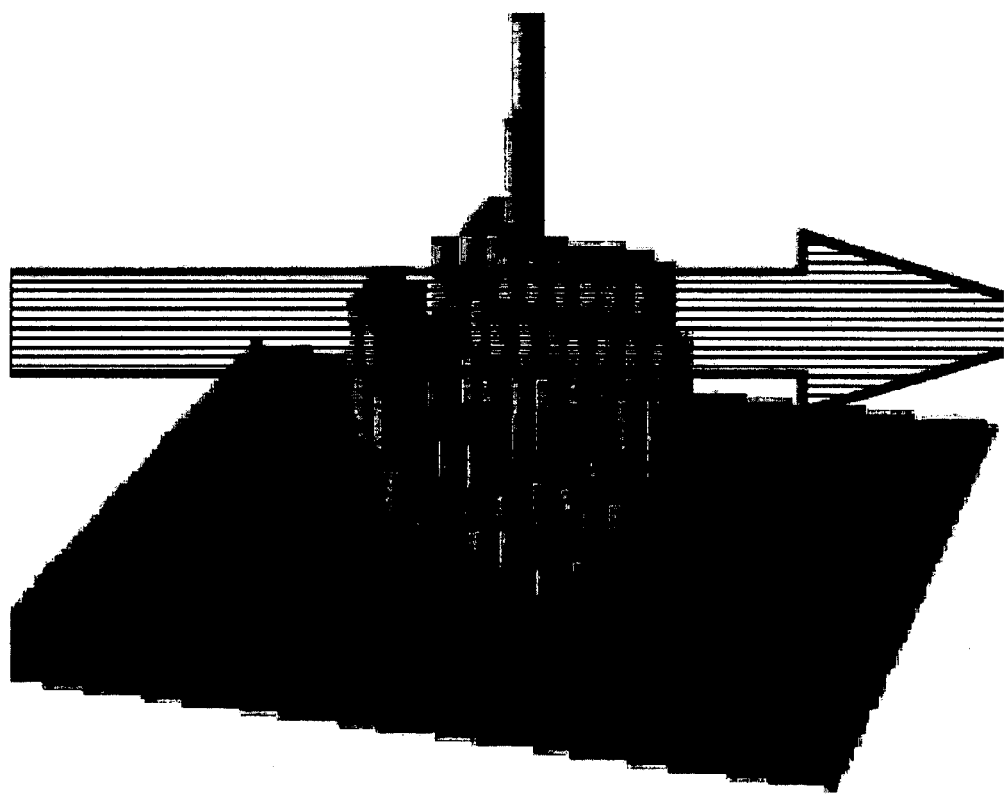
FIG. 2 is a discrete intensity map derived from the smooth intensity map of FIG. 1.
Figure 3:
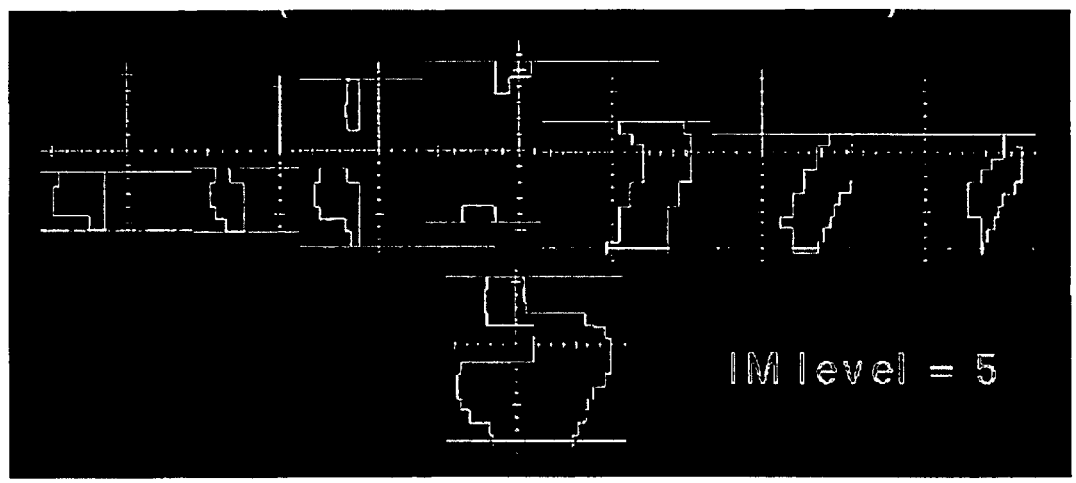
FIG. 3 is a series of segment fields delimited by multi-leaf collimator leaves for delivering an IMRT treatment.

In the present method, the actual MLC-IMRT treatment to be delivered to the patient is designed directly from the ideal intensity map Mo in the segmentation or segment-field generation process performed by the segmentation algorithm. This direct segmentation process differs from previous segmentation methods, which are characterized by requiring a discrete intensity map (i.e., a map consisting of 1 cm×1 cm blocks) or truncating the ideal continuous map into a corresponding discrete map (see, e.g., FIG. 2) before segmentation. The present method eliminates a source of inaccuracy that results from converting an ideal intensity map into a discrete map or from the lack of intensity modulation resolution in the dose optimization.

In accordance with the segmentation process of the present method, the MLC segment fields are designed sequentially, with each segment delivering a fraction of a residual intensity map, which is the intensity map still to be delivered after the preceding segments. This is accomplished by designing the MLC segments one at a time. After the configuration of a segment field is determined, the intensity map contribution from the segment field is calculated and subtracted from the intensity map to be delivered, thereby yielding a new residual map. The residual map is used to determine the next segment field configuration. Thus, the residual map diminishes with each iteration. This iterative segmentation process stops when the residual map is diminished to a predetermined intensity level, when a predetermined number of segments fields have been generated, and/or when other suitable stopping criteria have been met.

Figure 5:
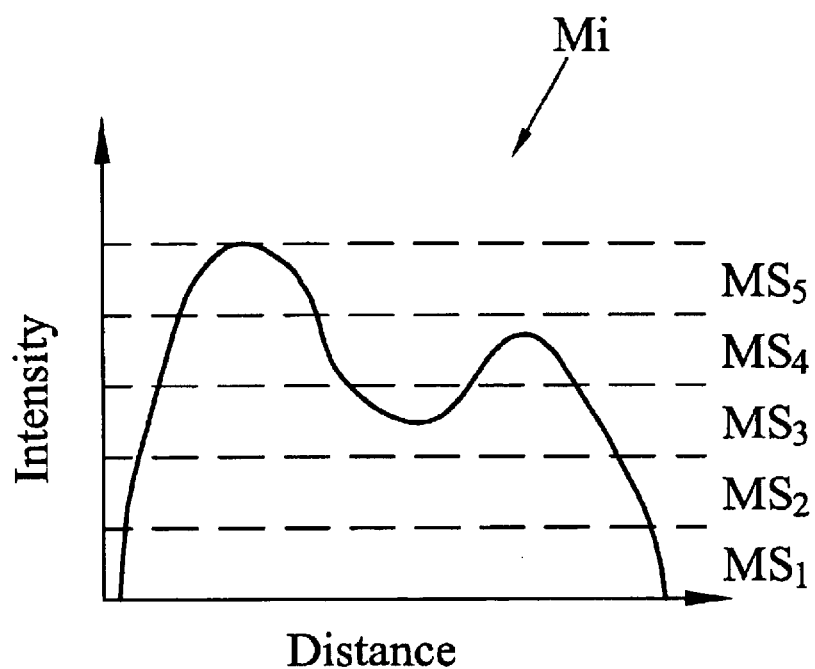
FIG. 5 is a two-dimensional representation of the ideal intensity map of FIG. 4, divided into map sections in accordance with the segmentation process disclosed herein.
Figure 11:
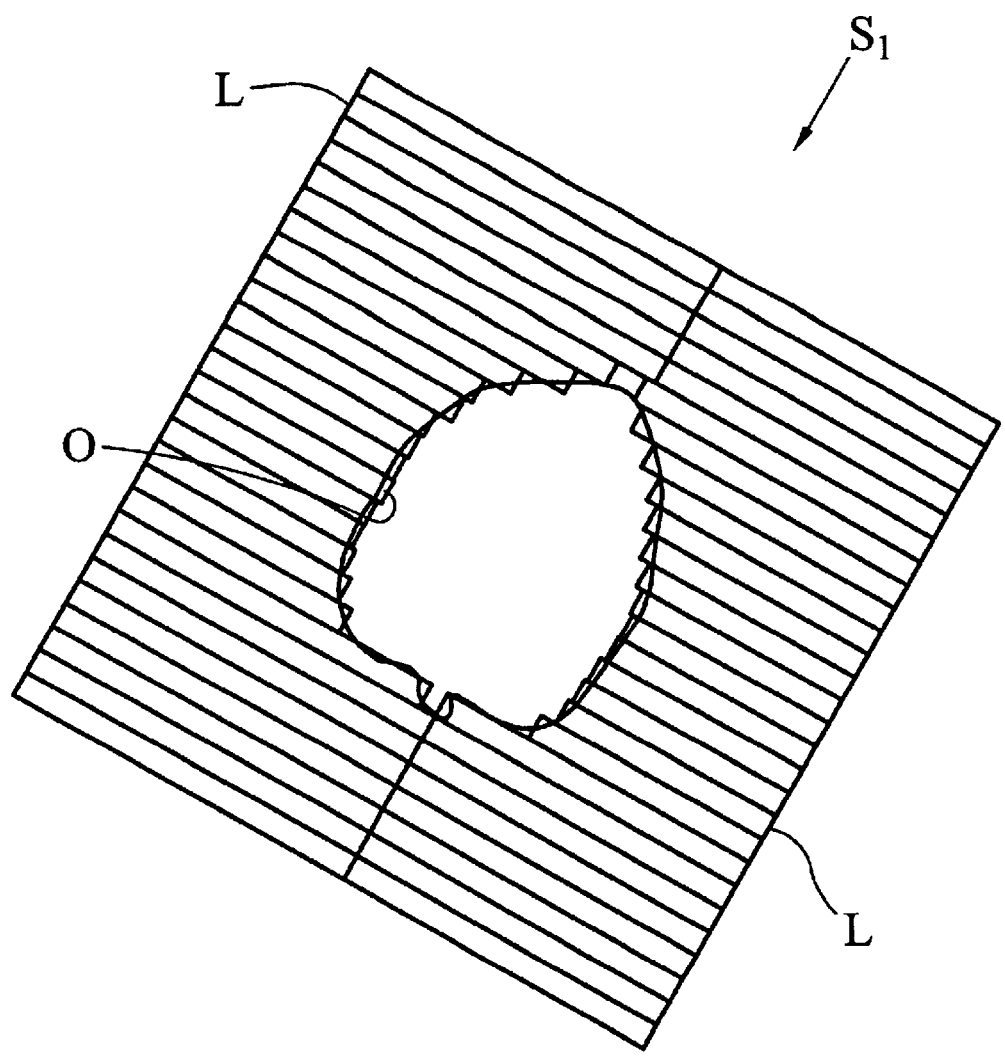
FIG. 11 is a top plan view of an example of a segment field configured from the ideal intensity map of FIG. 4 in accordance with a method disclosed herein.

More specifically, the MLC segments are designed by dividing the current inputted intensity map $M_i$ into (N-i) levels or map sections that can be delivered sequentially via MLC segments, where i=0, 1, ..., (N−1). The index value i represents the number of segment-fields created so far during the iterative process, and the integer value N represents the total number of segments to be created for the particular ideal map. Each map section has an equal height or intensity range. Thus, for the first iteration of this process, i=0 and the current intensity map $M_i$ is the ideal continuous map $M_0$, an example of which is shown in FIG. 4. If, for example, N is selected to have the integer value of 5, then the ideal continuous map $M_o$ is divided into (5-0), or 5, map sections. A two-dimensional example of a current intensity map $M_i$ (which, for this first iteration, is the ideal continuous map $M_0$) divided into 5 map sections $MS_1$–$MS_5$ along the intensity axis is shown in FIG. 5. Next, the lowest map section $MS_1$ of the ideal continuous map $M_0$ is selected, and the shape or contour of the upper opening of the map section $MS_1$ is defined mathematically. The upper opening O is depicted in FIG. 11, and defines the radiation portal that corresponds to the lowest-level intensity map section $MS_1$ shown in FIG. 5. The mathematical definition of the contour of the upper opening O is used to determine the positioning of the MLC leaves L (see FIG. 11) and thus the port or opening through which radiation would be delivered to the treatment field of the target, such as the tumor of a patient.

Once the lowest-level map section $MS_1$ has been defined, the MLC configuration is determined that best defines its contour, i.e., best defines the radiation portal geometrically. The MLC configuration is determined in terms of both the lateral positioning of the MLC leaves and their collimator angle. This determination optimizes the MLC orientation of each segment to increase the accuracy of the MLC segment-generated intensity fraction. For discrete MLC-IMRT techniques, the orientation of the MLC leaves can have a considerable influence on the quality and efficiency of the treatment. The present method also recognizes that MLC leaves can be translated to any position within their operating range to a great degree of accuracy (i.e., micro-scale). As indicated hereinabove, previous methods have not taken advantage of the continuous positioning capability of the MLC hardware of commercially available medical LINAC systems, but rather position MLC leaves by indexing them in 1-cm increments. The present method, on the other hand, takes full advantage of both the continuous MLC leaf positioning and the continuous collimator angle selection available in MLC-equipped radiotherapy machines. Optimization of collimator orientation assists in generating a more accurate intensity map with less required segment fields.

Figure 7A:
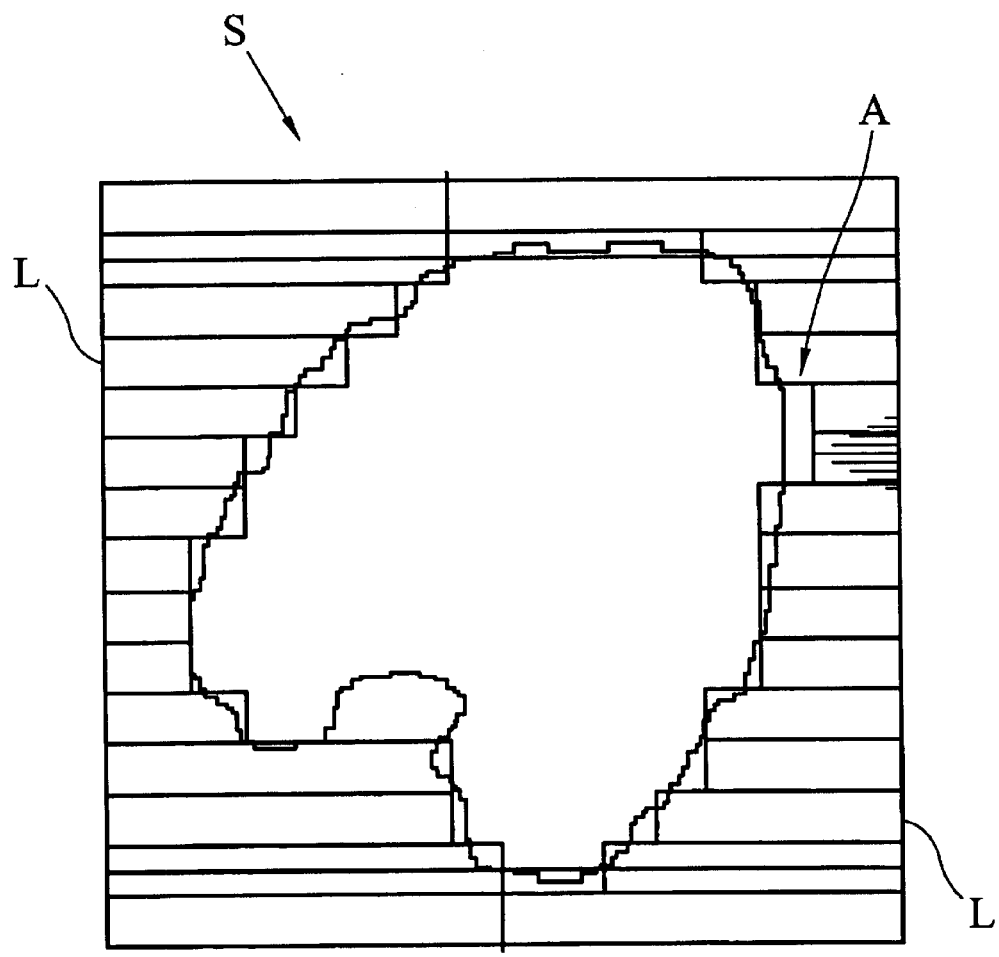
FIG. 7A is a top plan view of a segment field delimited by a multi-leaf collimator, wherein the leaves of the collimator have been positioned at a spatial resolution of 1 cm.
Figure 7B:
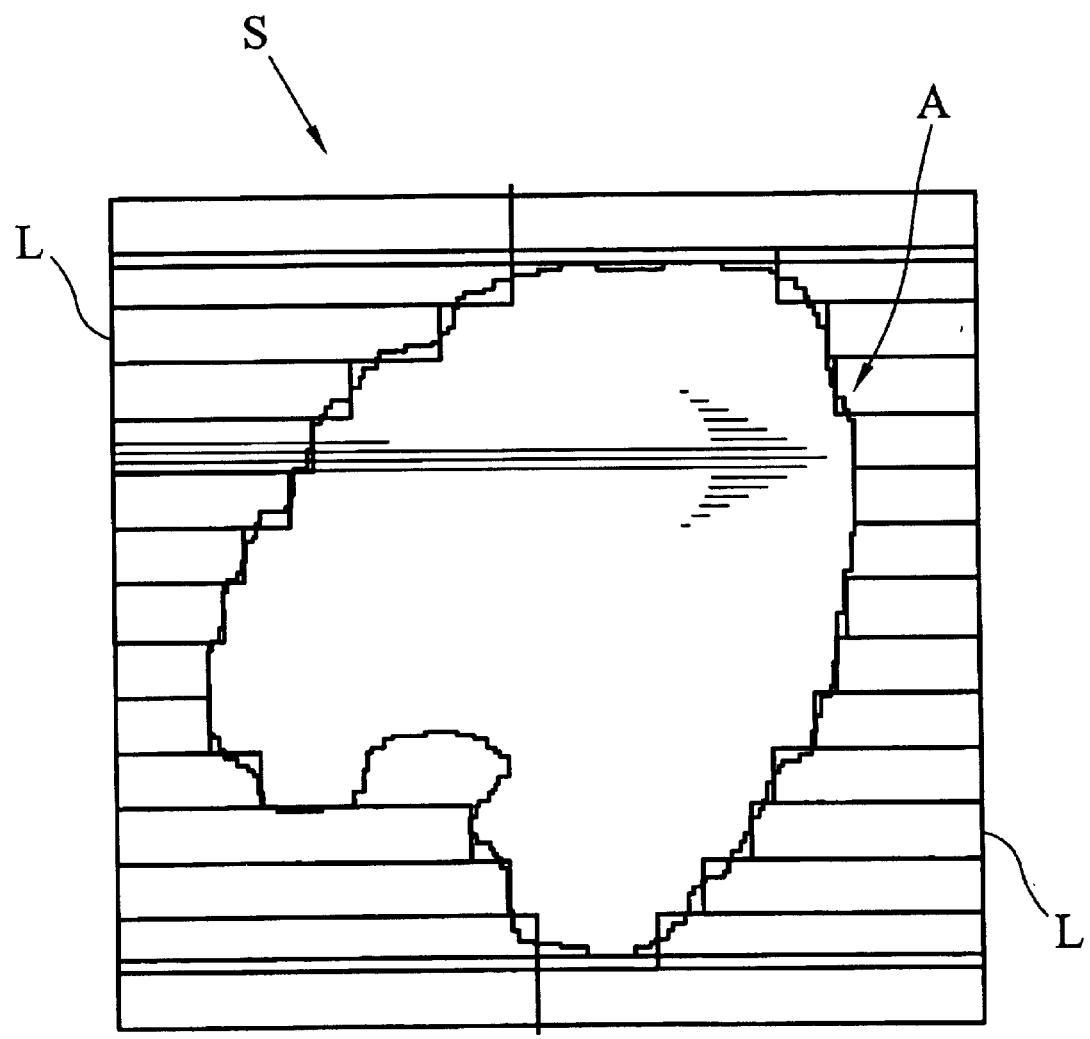
FIG. 7B is a top plan view of a segment field delimited by a multi-leaf collimator, wherein the leaves have been positioned on a continuous basis for better conformity as determined by a method disclosed herein.

Optimization of continuous MLC leaf positioning is shown in FIGS. 7A and 7B. FIGS. 7A and 7B demonstrate a comparison between the positioning of MLC leaves L in accordance with the conventional method for a given segment S (FIG. 7A), and the positioning of MLC leaves L in accordance with the present method for the same segment S (FIG. 7B). It can be seen in FIG. 7A that large discrepancies exist between the intended contour of the segment S and the actual contour realized by the MLC leaves. This is especially apparent at the location generally designated A. In FIG. 7B, as a result of the present method, a much closer match or conformity exists between the intended contour and the actual MLC leaf-defined contour. In particular, the location A in FIG. 7B now has a much better fit. The present method enables the positioning in FIG. 7B at least in part because calculations are based on a continuous intensity map $M_1$ (e.g., intensity map $M_0$ in FIG. 4), as opposed to a discrete intensity map (e.g., the map of FIG. 2) employed by conventional methods.

Figure 8A:
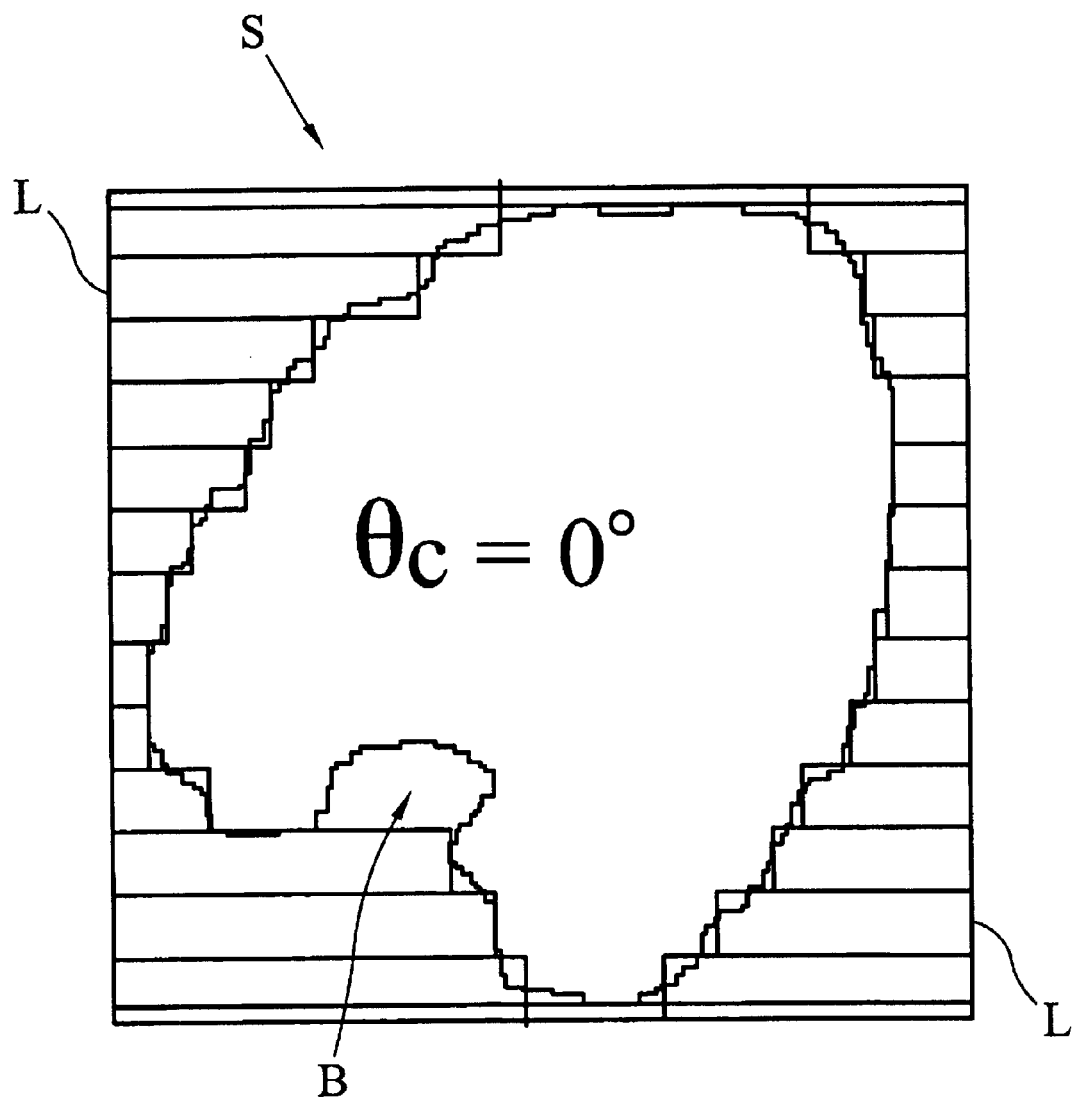
FIG. 8A is a top plan view of a segment field delimited by a multi-leaf collimator, wherein the leaves are oriented at a collimator angle of 0°.
Figure 8B:
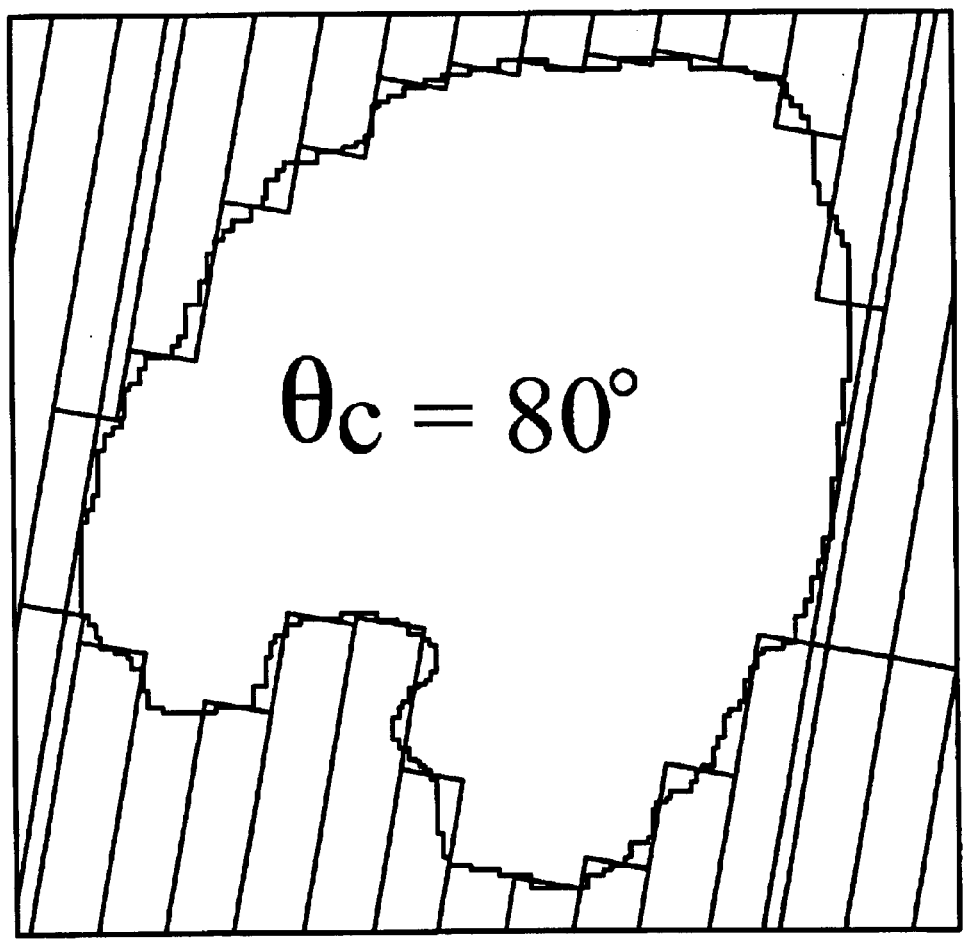
FIG. 8B is a top plan view of a segment field delimited by a multi-leaf collimator, wherein the leaves have been oriented at a collimator angle of 800 for optimal configuration as determined by a method disclosed herein.

Optimization of the collimator angle is shown in FIGS. 8A and 8B. FIGS. 8A and 8B demonstrate a comparison between the angular positioning of MLC leaves, or collimator angle $\theta_c$, in accordance with the conventional method for a given segment S (FIG. 8A), and the angular positioning in accordance with the present method for the same segment S (FIG. 8B). It can be seen in FIG. 8B that the present method has determined that a collimator angle of 80° provides the best match for this particular segment as compared with the collimator angle of 0° in FIG. 8A. This is particularly apparent at the cavity area of the segment S generally designated B in FIGS. 8A and 8B.

Figure 6:
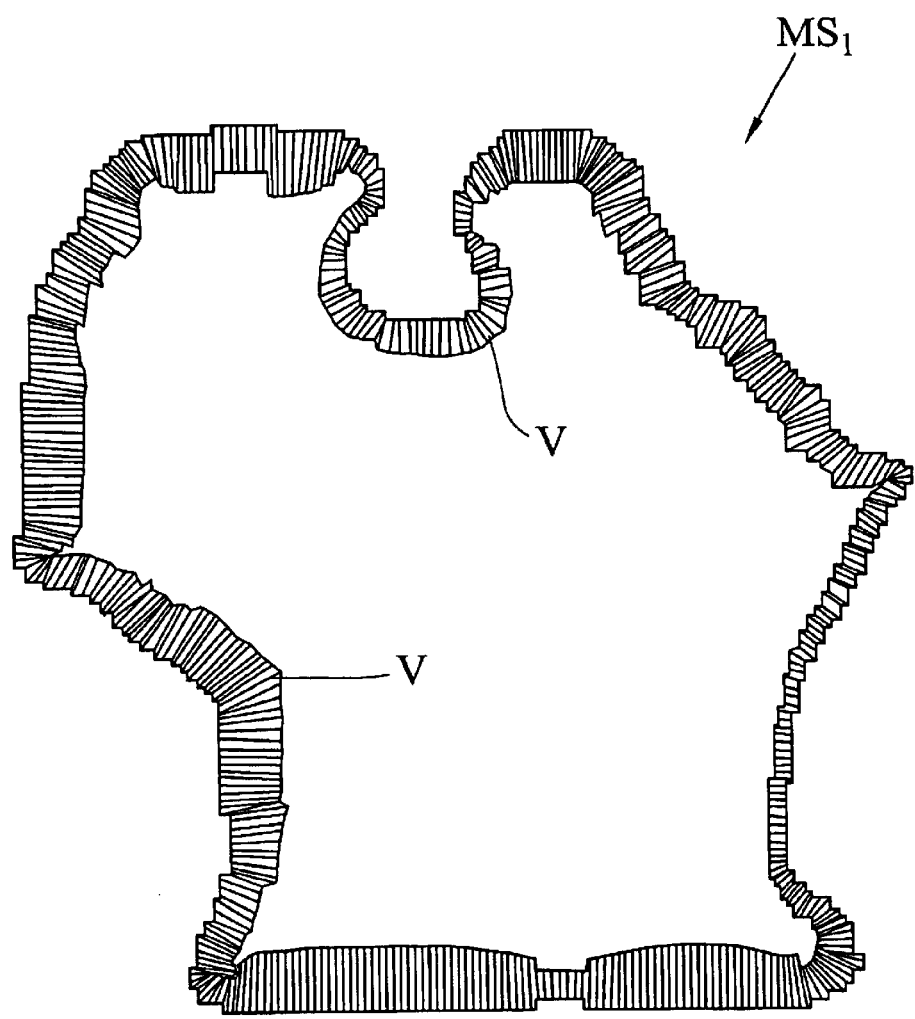
FIG. 6 is a top plan view of the lowest map section of FIG. 5, with gradient vectors drawn along its contour.
Figure 9:
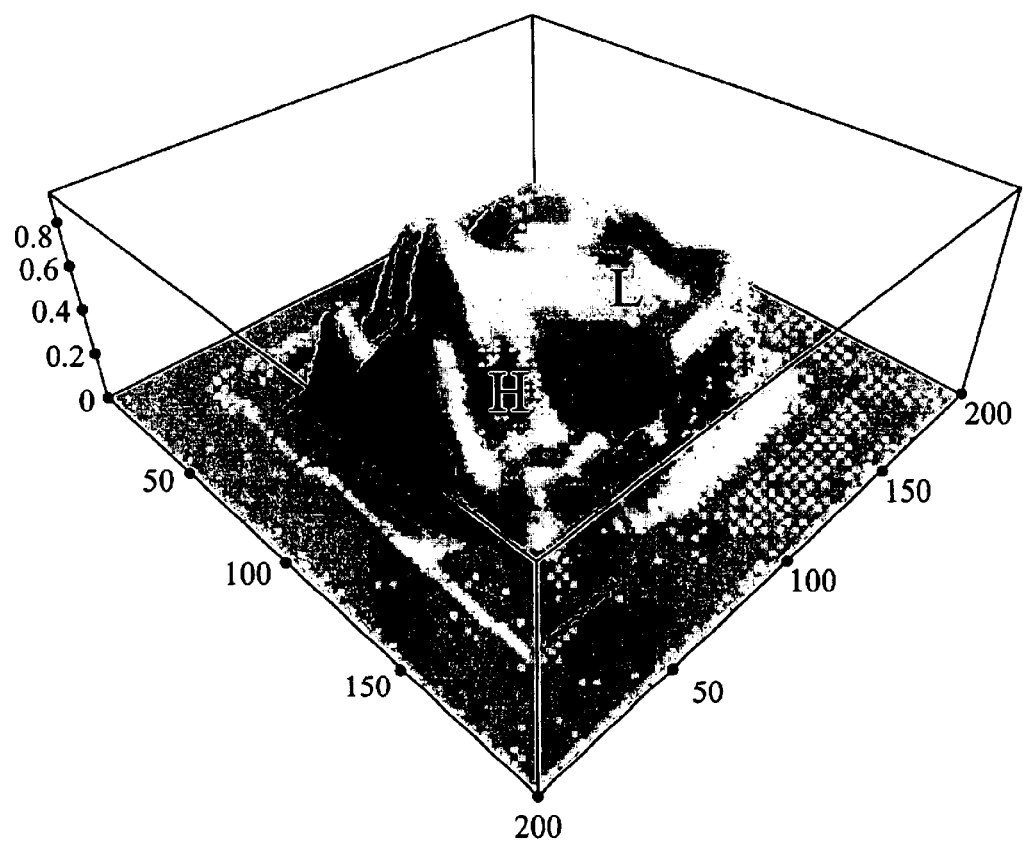
FIG. 9 is an ideal intensity map in which high-gradient and low-gradient regions have been identified.
Figure 10:
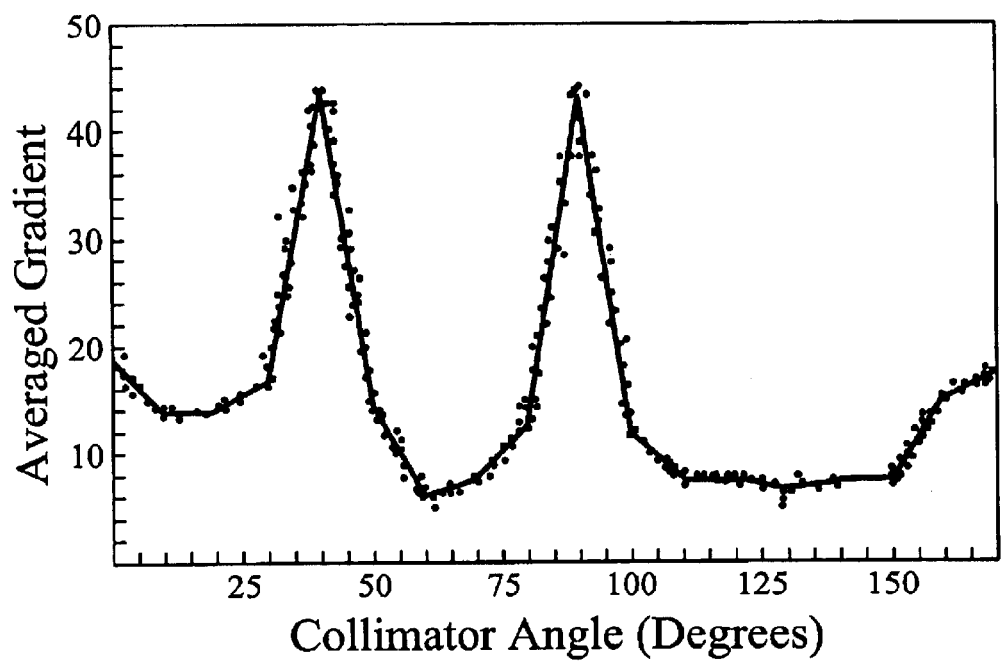
FIG. 10 is a plot of averaged gradient as a function of collimator angle, showing optimal collimator angles for better preservation of high-gradient regions of an intensity map in accordance with a method disclosed herein.

The present method provides two solutions or algorithms for searching for the optimal collimator angle for the MLC segment-field. The first solution finds the collimator angle that conforms to the contour as closely as possible, i.e., better definition of the intensity map. The segment S illustrated in FIG. 8B is representative of an output of the first solution. In addition, the present method can implement a second solution. The second solution searches for the optimal collimator angle that better preserves the high-gradient regions of the map section $MS_1$. As indicated hereinabove, the intended dose optimization objective is often generally expressed in terms of adequate dose coverage to the tumor while sparing the nearby normal structures at risk of radiation damage. In the present method, it is hypothesized that the objective, or the treatment quality, is more sensitive to the high-gradient regions of the intensity map than the low gradient regions. For example, FIG. 9 shows an intensity map in which a high gradient region has been designated H and a low gradient region has been designated L. For the present purposes, the "gradient" could be defined as the change in height of the intensity represented by the map relative to a change in position along the base plane. For each segment, the gradient of the intensity map is calculated, as indicated by the gradient vectors V drawn at the periphery of the map section $MS_1$ shown in FIG. 6. The direction and magnitude of the gradient at a given location is indicated by the direction and the length of the gradient vector V corresponding to that location, respectively. The second solution determines the collimator angle that allows the MLC leaves to be best defined the high-gradient areas of the intensity map. An example of the result of these calculations is shown in FIG. 10, which indicates that there are two good angles (approximately 45° and 80°) for a given segment.

The present method can be adapted for determining the MLC configuration for the given segment based on the solution of better definition of the intensity map/treatment portal alone, the solution of better preservation of the high gradient regions of the intensity map alone, a selection of one solution over the other, or a combination or weighting of both solutions. Each solution takes into account the ability of the radiation treatment hardware to finely adjust MLC leaf positions for optimal conformity, as described hereinabove with reference to FIGS. 7A and 7B. An optimal collimator angle can also be selected for all segments of the same IM field to increase treatment delivery efficiency. According to one aspect of the method, the final solution or solutions is chosen based the influence of such solution or solutions on treatment delivery efficiency. FIG. 11 illustrates the first segment $S_{1i}$ constructed from the first intensity map $M_0$ (FIG. 4) inputted into the segmentation process. The first segment $S_1$ has an optimal MLC configuration as a result of the methods just described.

Figure 12:
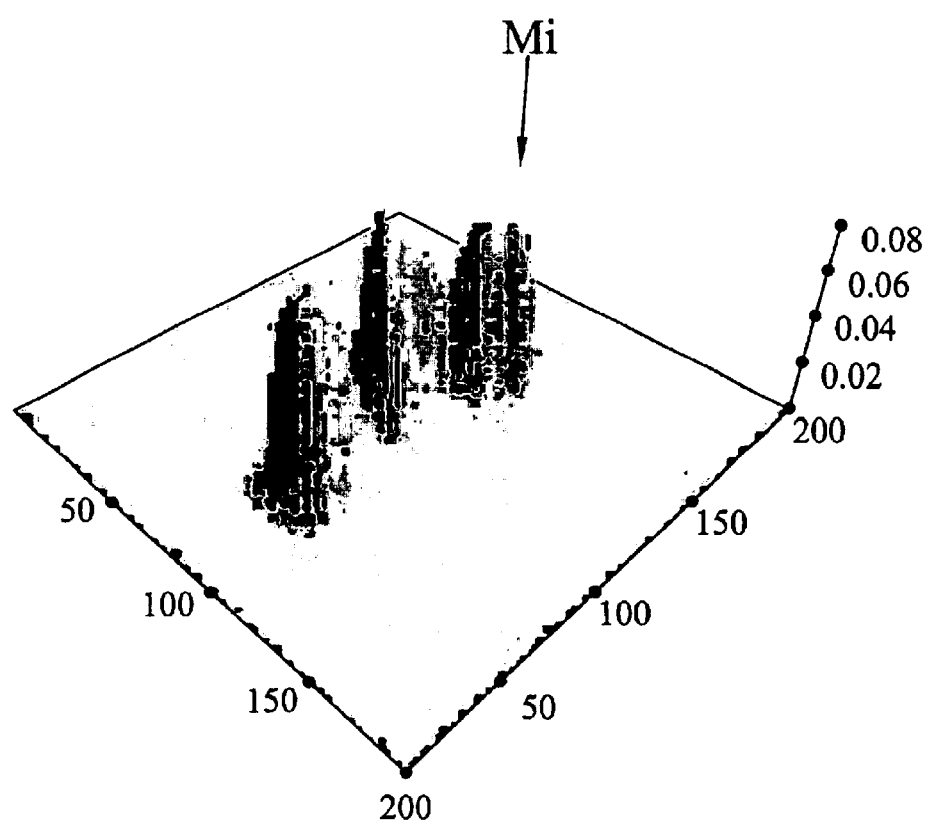
FIG. 12 is an example of an intensity map delivered by a segment field, as calculated in accordance with a method disclosed herein.

Once the MLC configuration for the current segment Si has been determined, including both MLC leaf positioning and collimator angle, the intensity map $m_{i1}$ generated by the resulting individual segment-field $S_i$ and its corresponding relative or absolute MU value are calculated, using the photon source model from the TPS where the ideal intensity map $M_0$ was created. If the photon source model describes the photon fluence change with accelerator collimator setting, the accelerator monitor unit needed for the segments to deliver the prescribed treatment dose can be calculated. As described hereinabove, each intensity map $m_i$ describes a fraction of the intensity described by the continuous intensity map $M_i$ input into the current iteration. For the first iteration the input intensity map is the ideal intensity map $M_o$. For subsequent iterations, the input intensity map is a residual intensity map $M_{i+1}$ as described hereinbelow. An example of an intensity map $m_i$ delivered by a segment $S_i$ is shown in FIG. 12.

Figure 13:
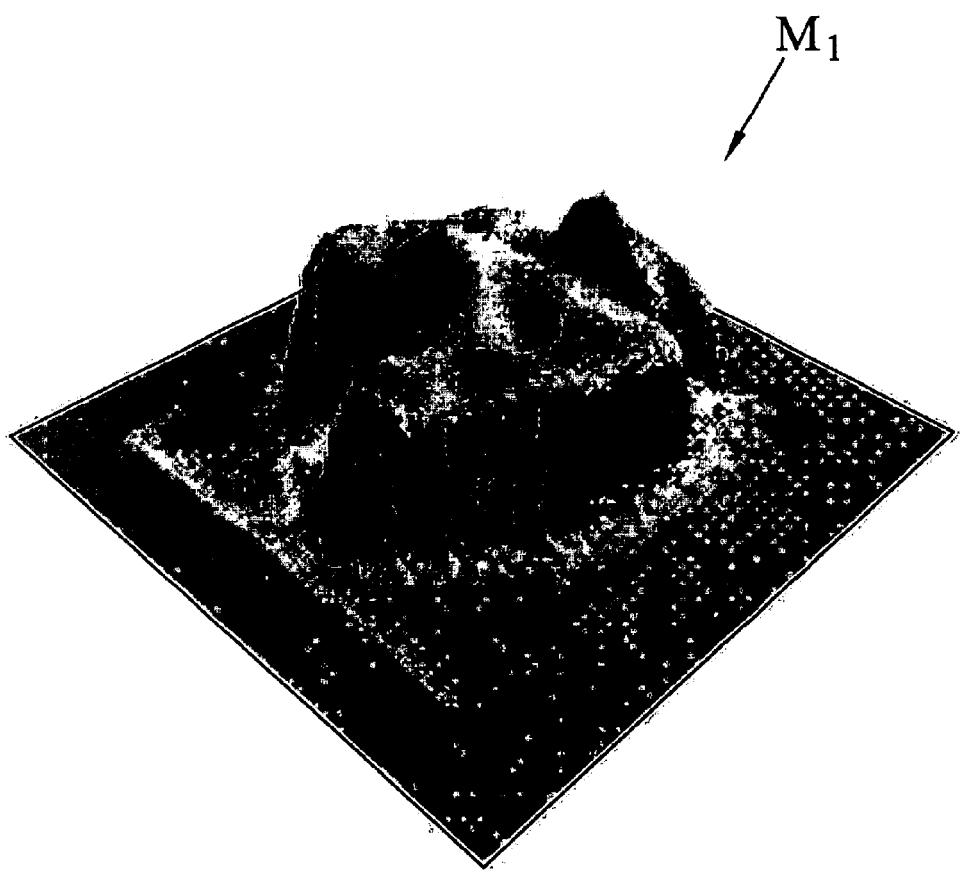
FIG. 13 is a an example of residual intensity map derived from the ideal intensity map of FIG. 4 and from a fractional intensity map, such as shown in FIG. 12, corresponding to the segment field of FIG. 11 in accordance with a method disclosed herein.
Figure 14:
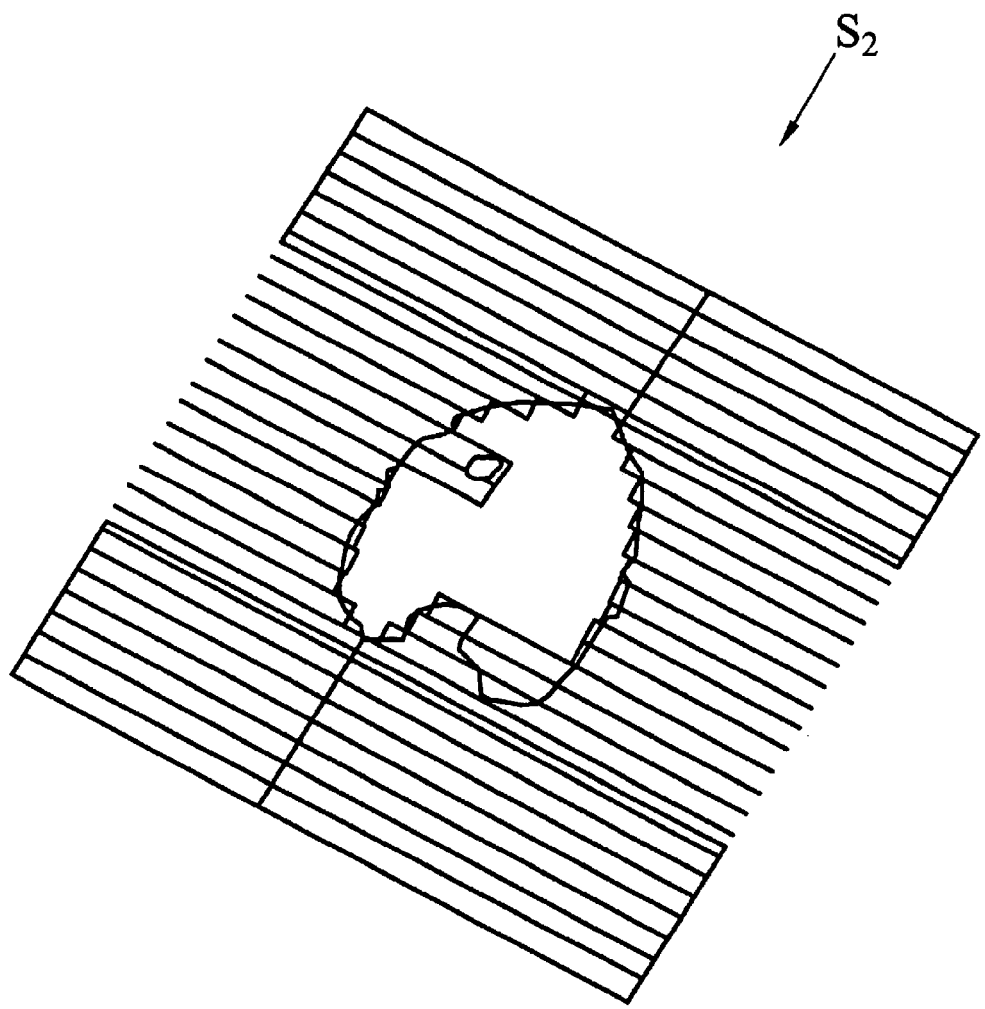
FIG. 14 is a top plan view of an example of a segment field derived from the residual intensity map of FIG. 13.
Figure 15:
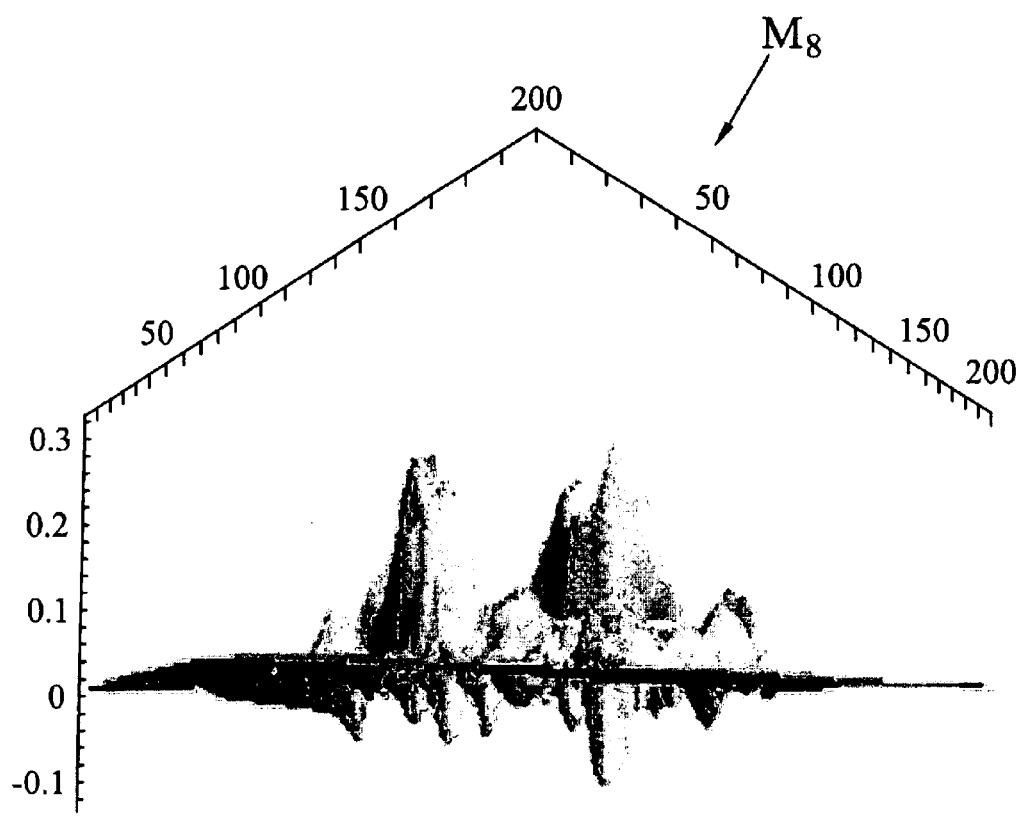
FIG. 15 is an example of a residual intensity map generated after eight segments have been configured in accordance with the method disclosed herein.
Figure 16:
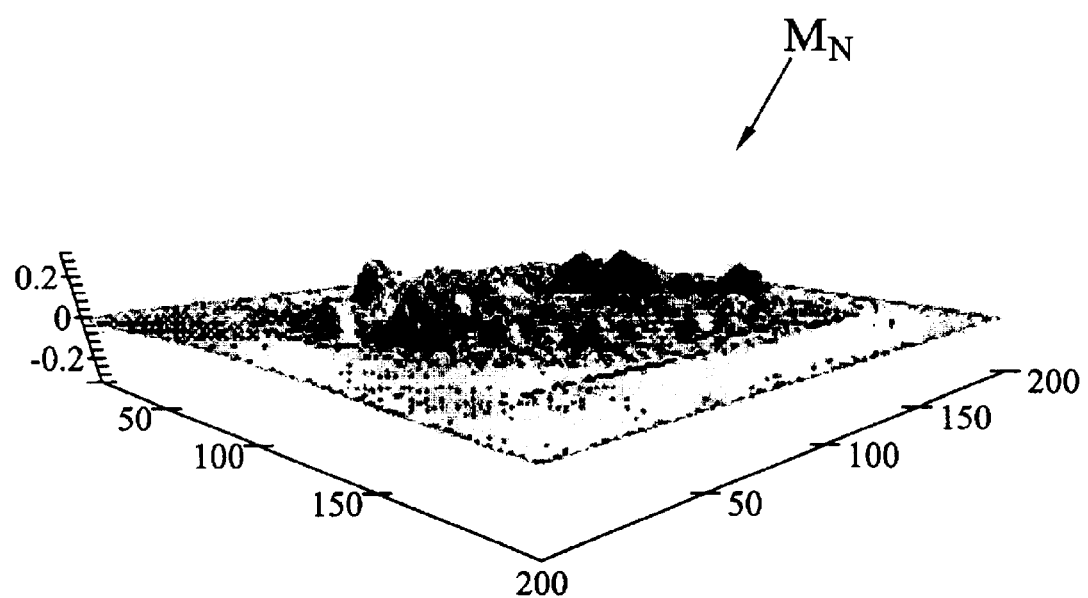
FIG. 16 is an example of a residual intensity map generated at the end of a segmentation process disclosed herein.

Next, a residual map calculation is performed, in which a residual map $M_{i+1}$ is obtained by subtracting the individual intensity map $m_i$ for the current segment $S_i$ from the current intensity map $M_i$ inputted at the beginning of the iterative process, according to the following equation: $M_{i+1}=M_I-m_I$. The resulting residual map $M_{i+1}$ represents the intensity map to be delivered by the remaining segment-fields. FIG. 13 illustrates a first residual map $M_1$ derived from the first iteration. After the residual map $M_{i+1}$ for the current iteration has been obtained, the method entails determining whether or not certain stopping or termination criteria have been met. In one aspect of the method, the stopping criteria include whether the maximum number of segment-fields, i, have been generated and whether the maximum amplitude designated for the residual maps has been reached. If either of these stopping criteria has not been met, the current residual map $M_{i+1}$ is inputted back into the iterative process to serve as the basis for determining the next segment field configuration. As examples, FIG. 14 illustrates the second segment $S_2$ constructed from the second intensity map inputted into the segmentation process (the residual map $M_1$ derived from the first iteration). FIG. 15 illustrates the residual map $M_8$ derived after eight segments have been configured during the segmentation process. The negative values of the residual map as shown in FIG. 15 indicate overdose to the patient, i.e., the intensity delivered by the segment is more than intended. The large overdose regions often are in the areas of the intensity map where the gradient is high. The overdose can be reduced by different approaches in MLC lead configuration. The negative valued regions on a residual map are truncated to zero in the segmentation process. FIG. 16 illustrates a final residual map $M_N$ derived after twelve segments.

If, on the other hand, one or more of the stopping criteria are met, the iterative process ends. At this point, if additional ideal intensity maps have been or need to be imported into the segmentation software, then the next ideal intensity map is then input into the iterative process as described above and the process begins anew. However, all ideal intensity maps could be processed simultaneously. For example, three ideal maps of an IMRT treatment can undergo segmentation in parallel.

One advantage of this residual map approach is that it is relatively forgiving. For instance, as long as an imperfection in designing a segment-field does not cause overdose, it is included in the next residual map and will be taken care of by next segments.

The design of MLC segment fields sequentially as described above differs from previous segmentation algorithms, which determine the configuration of all segment fields concurrently from a discretized version of the intended intensity map based on geometry alone. The problem with this previous approach is that assumptions must be made on the intensity map produced by the segment field. Inaccuracy in the assumption can lead to less than optimal segmentation and thus inferior results in the actual IMRT patient treatment.

As is evident from the foregoing description, the method disclosed herein is advantageously implemented by software that is compatible with or even integrated with a suitable TPS program. Accordingly, in one embodiment, a computer program product is provided that comprises computer-executable instructions embodied in a computer-readable medium for performing the steps of the method in accordance with the various aspects disclosed herein. As appreciated by persons skilled in the art, the software can be written in any suitable high- or low-level programming language. The computer-readable medium can be any suitable medium, such as a compact disk or a floppy disk loaded into an appropriate reading device of any suitable computing device such as a personal computer, or transmitted wirelessly or otherwise electronically to the computing device such as via a network or internet connection, or loaded on a removable or fixed memory of the computing device. Computer systems appropriate for using the computer program product disclosed herein are known to persons skilled in the art. One example of a suitable computer system is disclosed in U.S. Pat. No. 6,353,655, cited hereinabove.

Figure 17:
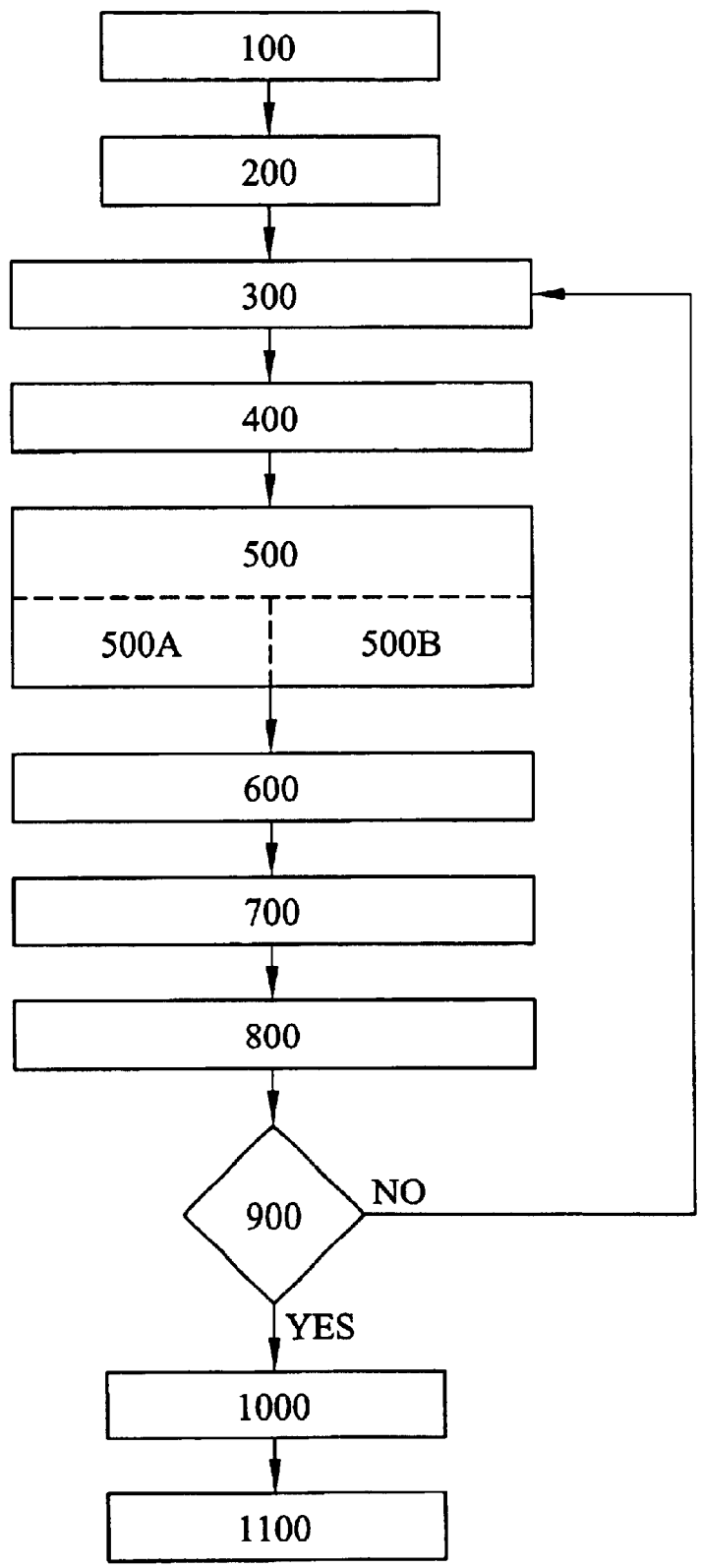
FIG. 17 is a flow chart illustrating a segmentation method disclosed herein.

The flow chart in FIG. 17 summarizes the present method which, as indicated herein, can be implemented in a computer program product. In step 100, the dose optimization is performed in treatment planning software to generate one or more ideal continuous intensity maps. In step 200, the ideal intensity maps are imported into the segmentation process or software. Steps 300–900 generally represent the segmentation process or software. As indicated hereinabove, segmentation process or software can be adapted to perform segmentations of each ideal intensity map in parallel. Accordingly, in the case of three ideal intensity maps for example, the flow chart in FIG. 17 could be visualized as including three parallel sets of steps 300–900, with each set of steps processing one of the ideal intensity maps imported into the process.

In step 300, each ideal intensity map $M_i$ is divided into (N-1) levels or map sections $MS_1$–$MSN_{N-1}$, where i=0 (ideal map), 1, . . . , (N-1). In step 400, the lowest map section $MS_1$ is selected, and the contour of its upper opening is defined. In step 500, the MLC configuration (i.e., the positioning of the MLC leaves and the collimator angle) is determined that best defines the contour of the lowest map section $MS_1$ defined in step 400. To reflect the ability to determine the MLC configuration using the two approaches or solutions described hereinabove, step 500 depicts substeps 500A and 500B, respectively. Sub-step 500A searches for the optimal collimator angle for the MLC segment-field that best conforms to the contour of the map section $MS_1$. Sub-step 500B searches for the optimal collimator angle that best preserves the high-gradient region of the map section $MS_1$. In step 600, the solution of either step 500A or 500B, or a combination of both steps, is chosen. This calculation results in the configuration of a segment $S_i$.

In step 700, the intensity map $m_i$ of segment $S_i$ and its MU value are calculated. In step 800, the residual map $M_{i+1}$ is calculated by subtracting the intensity map mi from the intensity map $M_i$ according to the relation $M_{i+1}=M_i-m_i$. In step 900, the process or software makes a query as to whether predetermined stopping criteria, examples of which are described hereinabove, have been met as a result of the current iteration. If the stopping criteria have not been met, the process loops back to step 300, where the residual map $M_{i+1}$ is divided into (N−1) levels (which, in the second iteration, would be N−2 levels), and the remaining steps 400–900 are repeated until the query point in step 900 is again reached. If, on the other hand, the stopping criteria have been met, the iterative process ends and control can pass, for example, to step 1000 where the information relating to the generated segments $S-S_N$ is transferred to the MLC hardware of a suitable radiotherapy treatment apparatus. Finally, step 1100 depicts the initiation of IMRT treatment of an object such as a tumor in accordance with the sequence of segments generated by the method.

The methods disclosed herein can be implemented in conjunction with any suitable radiotherapy treatment apparatus, such as the medical LINAC systems described in the patent references cited in the Background section hereinabove.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A method for generating a sequence of multi-leaf collimator segment fields for use in delivering intensity modulated radiotherapy without the use of discrete intensity maps, comprising the steps of:
    (a) generating a segment field directly from a continuous intensity map by determining an optimal collimator configuration corresponding to a contour of the continuous intensity map at a selected intensity level thereof;
    (b) calculating a fractional intensity map corresponding to the generated segment field; and
    (c) repeating steps (a) and (b) for one or more iterations to generate one or more additional segment fields wherein, for each iteration, the continuous intensity map used to determine the optimal collimator configuration of the additional segment field is derived in part from the fractional intensity map calculated in the previous iteration.

2. The method according to claim 1 wherein generating the segment field directly from the continuous intensity map comprises:
    (a) dividing the continuous intensity map into a plurality of map sections, each map section bounded by an intensity level of the continuous intensity map;
    (b) selecting the map section corresponding to the lowest intensity level and defining the contour of an upper opening of the selected map section; and
    (c) determining the optimal collimator configuration for the contour.

3. The method according to claim 2 wherein determining the optimal collimator configuration comprises determining respective lateral positions of the collimator leaves that best conform to the contour of the upper opening of the selected map section.

4. The method according to claim 2 wherein determining the optimal collimator configuration comprises determining an angle of the collimator leaves according to a first solution that best conforms to the contour of the upper opening of the selected map section.

5. The method according to claim 4 wherein determining the optimal collimator configuration comprises determining an angle of the collimator leaves according to a second solution that best preserves a high gradient region of the continuous intensity map.

6. The method according to claim 5 wherein the collimator angle is determined by considering both the first and second solutions.

7. The method according to claim 1 wherein determining the optimal collimator configuration comprises determining an angle of the collimator leaves that best preserves a high gradient region of the input intensity map.

8. A method for sequentially generating segment fields for use in delivering intensity modulated radiotherapy, comprising the steps of:
    (a) generating a segment field directly from an input continuous intensity map, wherein the segment field can define a collimator port configurable by collimator leaves through which a fraction of the continuous intensity map can be delivered to an irradiation target;
    (b) generating a residual continuous intensity map based on the respective photon fluence contributions from the input intensity map and a fractional intensity map corresponding to the segment field configured in step (a); and
    (c) repeating steps (a) and (b) for a number of iterations until one or more stopping criteria are met to generate additional segment fields and residual maps derived therefrom, wherein, in each iteration, the residual map generated in the previous iteration is used as the input intensity map.

9. The method according to claim 8 wherein, in a first iteration, the input intensity map is an ideal intensity map representing an ideal radiotherapy treatment.

10. The method according to claim 8 wherein, in a first iteration, the input intensity map is generated by a dose optimization process.

11. The method according to claim 8 wherein generating the segment field directly from the input intensity map comprises:
    (a) dividing the input intensity map into a plurality of map sections, each map section spanning an intensity range of the input intensity map;
    (b) selecting the map section corresponding to the lowest intensity range and defining a contour of an upper opening of the selected map section; and
    (c) determining an optimal collimator configuration that best defines the contour of the upper opening of the selected map section to configure the segment field corresponding to the optimal collimator configuration.

12. The method according to claim 11 wherein determining the optimal collimator configuration comprises determining respective lateral positions of the collimator leaves that best conform to the contour of the upper opening of the selected map section.

13. The method according to claim 11 wherein determining the optimal collimator configuration comprises determining an angle of the collimator leaves according to a first solution that best conforms to the contour of the upper opening of the selected map section.

14. The method according to claim 13 wherein determining the optimal collimator configuration comprises determining an angle of the collimator leaves according to a second solution that best preserves a high gradient region of the input intensity map.

15. The method according to claim 14 wherein the collimator angle is determined by considering both the first and second solutions.

16. The method according to claim 11 wherein determining the optimal collimator configuration comprises determining an angle of the collimator leaves that best preserves a high gradient region of the input intensity map.

17. The method according to claim 8 wherein the stopping criteria comprise whether a maximum number of segments have been generated.

18. The method according to claim 8 wherein the stopping criteria comprise whether the last residual map generated has a maximum amplitude.

19. A method for sequentially generating segment fields for use in delivering intensity modulated radiotherapy, comprising the steps of:
(a) dividing an input continuous intensity map derived from a dose optimization into a plurality of map sections, wherein each map section spans an intensity range of the input intensity map;
(b) selecting the map section corresponding to the lowest intensity range and defining a contour of an upper opening of the selected map section;
(c) determining an optimal collimator configuration that best defines the contour of the upper opening of the selected map section to configure a segment field corresponding to the optimal collimator configuration, wherein the segment field can define a collimator port configurable by collimator leaves through which a fraction of the continuous intensity map can be delivered to an irradiation target;
(d) calculating a fractional continuous intensity map contributed by the segment field;
(e) subtracting the fractional intensity map from the input intensity map to generate a residual continuous intensity map; and
(f) repeating steps (a)–(e) for a number of iterations until one or more predetermined stopping criteria are met, wherein, in each iteration, the residual intensity map generated in the previous iteration is used as a new input intensity map to configure a new segment field and generate a new residual intensity map.

20. The method according to claim 19 wherein, in a first iteration, the input intensity map is an ideal intensity map representing an ideal radiotherapy treatment.

21. The method according to claim 19 wherein, for each iteration, the input intensity map is divided into (N−i) map sections, where an iteration i=0, 1, . . . , (N−1) and N is the number of segment fields to be configured.

22. The method according to claim 19 wherein, for the first iteration, the input intensity map is an ideal intensity map.

23. The method according to claim 22 comprising the step of using a dose optimization process to generate the ideal intensity map.

24. The method according to claim 19 wherein determining the optimal collimator configuration comprises determining respective lateral positions of the collimator leaves that best conform to the contour of the upper opening of the selected map section.

25. The method according to claim 19 wherein determining the optimal collimator configuration comprises determining an angle of the collimator leaves according to a first solution that best conforms to the contour of the upper opening of the selected map section.

26. The method according to claim 25 wherein determining the optimal collimator configuration comprises determining an angle of the collimator leaves according to a second solution that best preserves a high gradient region of the input intensity map.

27. The method according to claim 26 wherein the collimator angle is determined by considering both the first and second solutions.

28. The method according to claim 19 wherein determining the optimal collimator configuration comprises determining an angle of the collimator leaves that best preserves a high gradient region of the input intensity map.

29. The method according to claim 19 wherein the stopping criteria comprise whether a maximum number of segments have been generated.

30. The method according to claim 19 wherein the stopping criteria comprise whether the last residual map generated has a maximum amplitude.

31. A computer program product comprising computer-executable instructions embodied in a computer-readable medium for performing steps comprising:
(a) importing a continuous intensity map derived from a dose optimization; and
(b) generating a segment field directly from the continuous intensity map by determining an optimal collimator configuration corresponding to a contour of the continuous intensity map at a selected intensity level thereof, wherein the segment field can define a collimator port configurable by collimator leaves through which a fraction of the continuous intensity map can be delivered to an irradiation target.

32. A computer program product comprising computer-executable instructions embodied in a computer-readable medium for performing steps comprising:
(a) importing an input continuous intensity map;
(b) generating a segment field directly from the input intensity map, wherein the segment field can define a collimator port configurable by collimator leaves through which a fraction of the continuous intensity map can be delivered to an irradiation target;
(c) generating a residual continuous intensity map based on the respective photon fluence contributions from the input intensity map and a fractional intensity map corresponding to the segment field configured in step (b); and
(d) repeating steps (b) and (c) for a number of iterations to generate a like number of additional segment fields and residual maps derived therefrom, wherein, in each iteration, the residual map generated in the previous iteration is used as the input intensity map.

33. A computer program product comprising computer-executable instructions embodied in a computer-readable medium for performing steps comprising:
(a) dividing an input continuous intensity map derived from a dose optimization into a plurality of map sections, wherein each map section spans an intensity range of the input intensity map;
(b) selecting the map section corresponding to the lowest intensity range and defining a contour of an upper opening of the selected map section;

(c) determining an optimal collimator configuration that best defines the contour of the upper opening of the selected map section to configure a segment field corresponding to the optimal collimator configuration, wherein the segment field can define a collimator port configurable by collimator leaves through which a fraction of the continuous intensity map can be delivered to an irradiation target;

(d) calculating a fractional continuous intensity map contributed by the segment field;

(e) subtracting the fractional intensity map from the input intensity map to generate a residual continuous intensity map; and (f) repeating steps (a)–(e) for a number of iterations until one or more predetermined stopping criteria are met, wherein, in each iteration, the residual intensity map generated in the previous iteration is used as a new input intensity map to configure a new segment field and generate a new residual intensity map.

* * * * *